United States Patent
Randel

(10) Patent No.: US 11,311,589 B2
(45) Date of Patent: *Apr. 26, 2022

(54) CANNABINOIDS INFUSED COFFEE BEANS AND RAW NUTS

(71) Applicant: Michael William Randel, Lakebay, WA (US)

(72) Inventor: Michael William Randel, Lakebay, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/404,280

(22) Filed: Aug. 17, 2021

(65) Prior Publication Data

US 2022/0096583 A1    Mar. 31, 2022

Related U.S. Application Data

(63) Continuation-in-part of application No. 17/039,787, filed on Sep. 30, 2020.

(51) Int. Cl.
| | |
|---|---|
| *A61K 36/00* | (2006.01) |
| *A61K 36/185* | (2006.01) |
| *A61K 47/44* | (2017.01) |
| *A61K 47/46* | (2006.01) |
| *A61K 9/00* | (2006.01) |
| *A23F 5/14* | (2006.01) |
| *A23L 33/105* | (2016.01) |

(52) U.S. Cl.
CPC .............. *A61K 36/185* (2013.01); *A23F 5/14* (2013.01); *A23L 33/105* (2016.08); *A61K 9/0056* (2013.01); *A61K 47/44* (2013.01); *A61K 47/46* (2013.01); *A23V 2002/00* (2013.01); *A61K 2236/31* (2013.01); *A61K 2236/35* (2013.01); *A61K 2236/37* (2013.01); *A61K 2236/53* (2013.01)

(58) Field of Classification Search
None
See application file for complete search history.

(56) References Cited

U.S. PATENT DOCUMENTS

| | | |
|---|---|---|
| 10,028,987 B1 | 7/2018 | Pillsbury |
| 10,103,225 B2 | 10/2018 | Reillo et al. |
| 2017/0196923 A1 | 7/2017 | Moore |
| 2018/0200315 A1 | 7/2018 | Silver |

FOREIGN PATENT DOCUMENTS

CA    2859930 A1    3/2016

*Primary Examiner* — Michael V Meller
(74) *Attorney, Agent, or Firm* — Thomas LaGrandeur

(57) ABSTRACT

The present disclosure is directed to whole spectrum cannabinoids infused coffee beans or raw nuts and methods of producing the cannabinoids infused coffee beans or raw nuts. The coffee beans or raw nuts are infused in an overall two-step process, in which cannabinoids from a *Cannabis* species are first infused into coconut oil, which in turn is used to infuse coffee beans or raw nuts with cannabinoids to generate the cannabinoids infused coffee beans or raw nuts.

18 Claims, 3 Drawing Sheets

CANNABINOIDS INFUSED COFFEE BEANS AND RAW NUTS

CROSS-REFERENCE TO RELATED APPLICATION

This application is a Continuation-in-Part that claims the benefit of U.S. application Ser. No. 17/039,787 filed on Sep. 30, 2020, which is incorporated by reference in its entirety.

FIELD OF THE INVENTION

The invention relates to *cannabis* whole spectrum cannabinoids that are infused into coconut oil, which in turn is used to infuse coffee beans or raw nuts with whole spectrum cannabinoids.

BACKGROUND

*Cannabis* has been used to alleviate stress and other illnesses caused by posttraumatic stress disorder, seizures, epilepsy, multiple sclerosis, and the like. *Cannabis*, commonly known as marijuana or hemp, is a genus of flowering plants that includes at least three species, *Cannabis sativa*, *Cannabis indica*, and *Cannabis ruderalis*.

*Cannabis* plants produce a variety of potentially useful or beneficial cannabinoids, which produce mental and physical effects when consumed. Cannabinoids are a chemical group or family of 21-carbon-containing terpenophenolic compounds produced by *Cannabis* species. Current estimates of the number of cannabinoids found in *Cannabis* species is well in excess of 100 different cannabinoids. Two of the most prominent cannabinoids are Cannabidiol (CBD) and Tetrahydrocannabinol (THC). In addition to CBD and THC, other cannabinoids such as cannabichromene (CBC), cannabigerol (CBG), cannabinol (CBN), and others are present in varying amounts in *cannabis* plant material.

Commonly consumed sources of cannabinoids include extracts, oils, isolates, and the like from *Cannabis* species including marijuana, hemp, and industrial hemp, which contains a THC content of less than 0.3% of overall mass. While providing useful or beneficial effects to the user, such extracts, oils, and isolates are typically found to have undesirable tastes, flavors, odors, and/or other unfavorable attributes. Accordingly, addition of cannabinoid containing extracts or isolates to food or beverage consumables imparts an undesirable taste, since the extracts or isolates typically have an undesirable taste. In particular, cannabinoids from extracts or isolates have been added to coffee for consumption in a beverage. The addition of cannabinoid containing extracts or isolates to coffee typically imparts an undesirable taste to coffee, since the extracts or isolates typically have an undesirable taste.

Accordingly, there exists a need in the art for consumable cannabinoids containing coffee beans and resultant beverages that do not have the tastes and odors of typically consumed sources of cannabinoid(s). Likewise, there exists a need for pleasant tasting, cannabinoids containing raw nuts. The presently disclosed cannabinoids infused coffee beans and raw nuts along with methods of preparing such coffee beans and raw nuts addresses these needs.

SUMMARY

The present disclosure provides for orally ingestible, cannabinoids infused coffee beans and raw nuts along with methods of producing such. The infused coffee beans in turn may be used for producing consumable coffee beverages.

The overall method disclosed entails a two-step process in which coconut oil is first infused with whole spectrum cannabinoids from a species of *Cannabis*. In the second step, the cannabinoids infused coconut oil is used to infuse coffee beans or raw nuts to generate whole spectrum cannabinoids infused coffee beans or raw nuts. The cannabinoids infused coffee beans can be used to generate a cannabinoids infused coffee beverage.

An overall preferred embodiment of generating cannabinoids infused coffee beans or raw nuts is presented herein. As detailed below, the method involves a series of steps of heating and freezing coffee beans or raw nuts in the presence of cannabinoids infused oil, such as coconut oil, to produce cannabinoids infused coffee beans or raw nuts.

The presently disclosed cannabinoids infused coffee beans and raw nuts are more fully described in the detailed description below.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF EXEMPLARY EMBODIMENTS

As is known in the art, cannabinoids are a class of chemical compounds found in plants in the *cannabis* family (e.g., hemp, marijuana, etc.). To date, more than 100 cannabinoids have been identified, accounting for up to 40% of the plant's extract. Well known cannabinoids include Cannabidiol (CBD), Tetrahydrocannabinol (THC) among others, each of which may include a variety of health benefits.

The present disclosure provides for coffee beans (along with resultant coffee beverages) and raw nuts that provide a source of whole spectrum cannabinoids, as well as methods of making such coffee beans and raw nuts. The presently disclosed coffee beans or raw nuts are infused with cannabinoids in a way that provides high levels and quantities of cannabinoids transferred to the coffee beans or raw nuts while reducing undesirable tastes, flavors, odors, and the like typically associated with and found in commonly used cannabinoid extracts, oils, isolates, edibles, and such.

As used herein, the term "infused cannabinoids" or "cannabinoids infused" refers to raw nuts or coffee beans and/or coffee beverages to which whole spectrum cannabinoids from *cannabis* have been infused by a method(s) disclosed herein. The infusion method generally involves preparing a mixture made with whole *cannabis* plant materials and coconut oil (or similar oil) under specific heating and cooling conditions to produce whole spectrum cannabinoids infused oil, and then in turn using the cannabinoids infused oil to infuse coffee beans or raw nuts as detailed herein. Throughout this specification, cannabinoids infused food and/or drink may be referred to as "cannabinoids infused" or simply "infused," such as "cannabinoids infused coffee beans" or "infused coffee beans."

Figure 1:
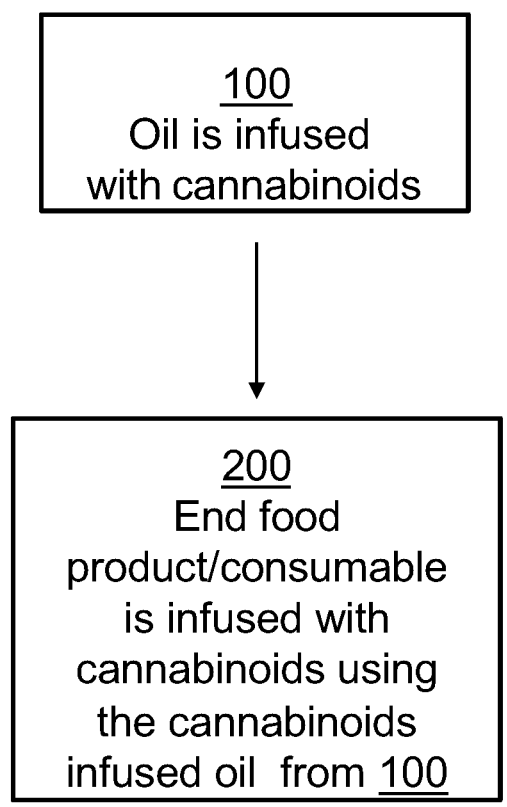
FIG. 1 shows example steps of a method according to exemplary embodiments hereof.

In some embodiments as shown in FIG. 1, cannabinoids infused coffee beans or raw nuts prepared by the methodology disclosed herein are generated in an overall two-step process. In the first step (at 100), whole *cannabis* plant material, preferably small buds, is used to infuse an oil, preferably coconut oil, with cannabinoids. Alternatively, whole *cannabis* plant material that has been ground can be used to infuse an oil. Note that because whole *cannabis* plant material is used at 100, the resulting infusion of the oil from the *cannabis* provides a full spectrum of cannabinoids from the *cannabis* to the oil. In a second step (at 200), the whole spectrum cannabinoids infused coconut oil is used to infuse coffee beans or raw nuts with cannabinoids. After the coffee beans are infused with cannabinoids, the coffee may be consumed in any typical fashion, such as direct consumption of the infused coffee beans or more typically, to a make an infused coffee beverage. Likewise, the cannabinoids infused raw nuts can be consumed directly or added to other foods, such as baked goods, to provide whole spectrum cannabinoids to the food.

Consumption of the cannabinoids infused coffee beans, coffee beverages, or raw nuts generated by the methods described herein provides the beneficial effects generally associated with cannabinoids. These effects include, but are not limited to, mental and physical effects, such as pain relief from CBDs and other cannabinoids, mental high from THC (in foods infused with marijuana cannabinoids), and other effects attributed to consumption of cannabinoids.

Figure 2:
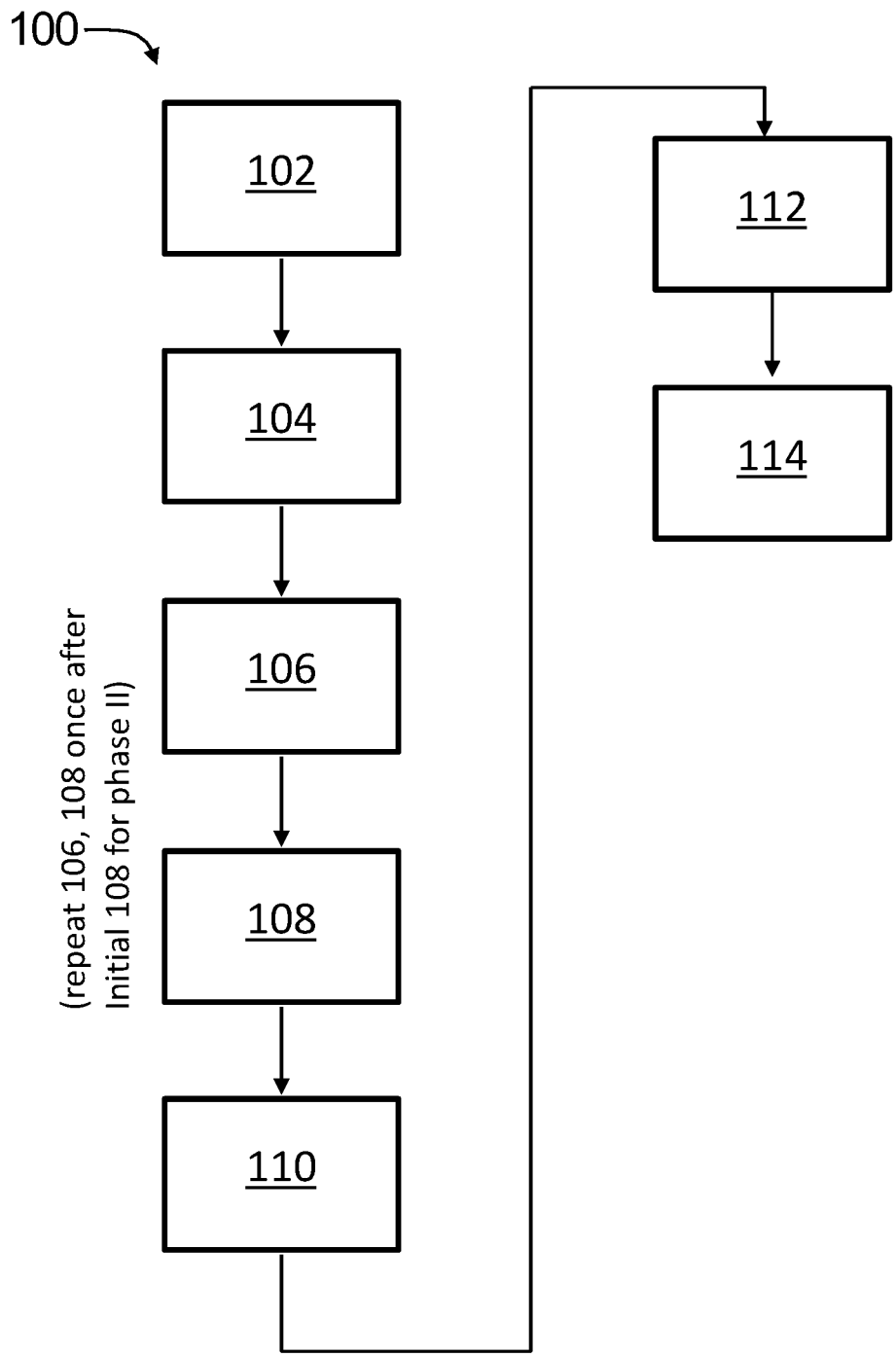
FIG. 2 shows example steps of a method according to exemplary embodiments hereof.

FIG. 2 refers to steps that may be taken to infuse a food grade oil (e.g., coconut oil, medium chain triglycerides (MCT) oil or a combination of coconut oil and MCT oil) with cannabinoids to complete step 100 of FIG. 1. Additional oils that can be used in the process include vegetable oil, sunflower oil, olive oil, grape seed oil and combinations thereof. Likewise, butter, shortening, margarine, or lard may be used in the process.

In one embodiment as shown in FIG. 2, whole, raw *cannabis* plant material (e.g., flowers, buds, leaves or other plant material; preferably small buds) is frozen (at 102). The *cannabis* plant may include *Cannabis Sativa, Cannabis Indica, Cannabis Ruderalis*, other types of *cannabis* and any combination thereof. The *cannabis* may be classified as marijuana, hemp, and/or other types of *cannabis*.

The *cannabis* plant material may also be a strain that is particularly rich in one or more specific cannabinoids, such as a strain that is particularly rich in cannabidiol (CBD) or cannabigerol (CBG). In addition, the *cannabis* plant material may be a combination of two or more different strains that are particularly rich for a specific cannabinoid. Currently available *Cannabis* strains are typically rich in CBD, but strains that are rich for other cannabinoids have been and are being developed. For example, more recently developed strains include those that are rich in CBG. Generally, cannabigerol (CBG) and cannabigerolic acid (CBGA) only account for 1% of a hemp strain's total cannabinoids. In a CBG-rich hemp strain, cannabigerol makes up around 10-15% or more of the *cannabis* flower's total cannabinoids. In a preferred embodiment, the *cannabis* plant material used in the presently disclosed method(s) is a mixture of equal parts of two strains that are rich in CBD and CBG, respectively. Additional strains that are particularly rich in a specific cannabinoid and combinations thereof fall within the scope of the presently disclosed method(s).

Next (at 104), coconut oil, MCT oil, a combination of coconut oil and MCT oil (or similar oil) is heated to a temperature equal to or between 150° and 200° F., and preferably to about 185° F. For the purposes of this specification, the term "about" used in relation to temperatures will mean within ±1%. Regarding a combination of coconut oil and MCT oil, a preferred embodiment is to use a ratio of 75% coconut oil to 25% MCT oil. Alternatively, ratios of coconut oil to MCT oil can range from 90% coconut oil: 10% MCT to 75% coconut oil: 25% MCT oil.

Next (at 106), the frozen *cannabis* (preferably small buds) is added to the coconut oil and held at the temperature (e.g., preferably at about 185° F.) for 5-7 hours, while occasionally (and/or continuously) stirring the mixture. In some embodiments, the ratio of plant material to coconut oil is 1 lb plant material to 2 gallons oil. For example, on a commercial scale, 100 lbs plant material/buds may be mixed with 200 gallons of oil. However, other ratios within 10%, 20%, 30%, 40%, 50%, 75%, 100% of this ratio also may be used. In general, the ratio will be chosen to provide high levels/concentration(s) of cannabinoids within the oil.

After the heating step of 106, in the next step (at 108), the *cannabis* and coconut oil mixture is frozen to obtain a solid, frozen biomass of *cannabis* and coconut oil mixture.

At this juncture, the solid, frozen biomass of *cannabis* and coconut oil can be processed in one of two ways. First, the *cannabis* and coconut oil can be heated and strained as per steps 110, 112, and 114 to yield cannabinoids infused coconut oil produced by a single round or phase of heating and freezing. Second, the *cannabis* and coconut oil alternatively can be treated with a second round or phase of heating and freezing, in which steps 106 and 108 are repeated, followed by subsequent steps 110, 112, and 114 to yield cannabinoids infused coconut oil produced by two rounds of heating and freezing. The single round/phase treatment will produce cannabinoids infused coconut oil having about a 50% relative level of infused cannabinoids compared to a double round/phase treatment that will produce cannabinoids infused coconut oil having about an arbitrary 100% relative level of infused cannabinoids. The double round/phase treatment has been found to provide maximal levels of cannabinoids infused into the coconut oil, which are arbitrarily referred to as 100% levels of infused cannabinoids. The single round/phase treatment can produce cannabinoids-infused coconut oil that is adequate for many applications. If higher infused levels of cannabinoids in coconut oil are desired for a particular application, the double round/phase treatment of cannabinoids infused coconut oil can be applied.

Following step 108, at step 110, the solid, frozen *cannabis* and coconut oil biomass is reheated to 150° to 200° F., and preferably to about 185° F., and held at the temperature for a sufficient period of time to liquefy the mixture, typically for about 2-4 hours.

Next (at 112), the *cannabis* and coconut oil mixture is strained using a press bag (or other suitable straining techniques) to separate the cannabinoids infused coconut oil from the *cannabis* biomass.

In a further step (114), the strained, cannabinoids infused oil is heated to between 250° F. to 300° F. for 3-6 hours. This step will decarboxylate the carboxylated cannabinoids in the oil, such as CBD-A or THC-A. The temperature and time will vary based in part on the *cannabis* strain used and desired decarboxylation. For example, using a CBD-rich strain that provides high levels of CBD-A, the step will preferably include a temperature of 250° F. for 3-6 hours. In another example, using a CBG-rich strain that provides high levels of CBG-A, the step will preferably include a temperature of 300° F. for 3-6 hours.

This method results in a whole spectrum cannabinoids infused coconut or other oil that may be used for infusing coffee beans or raw nuts with cannabinoids as described below.

Figure 3:
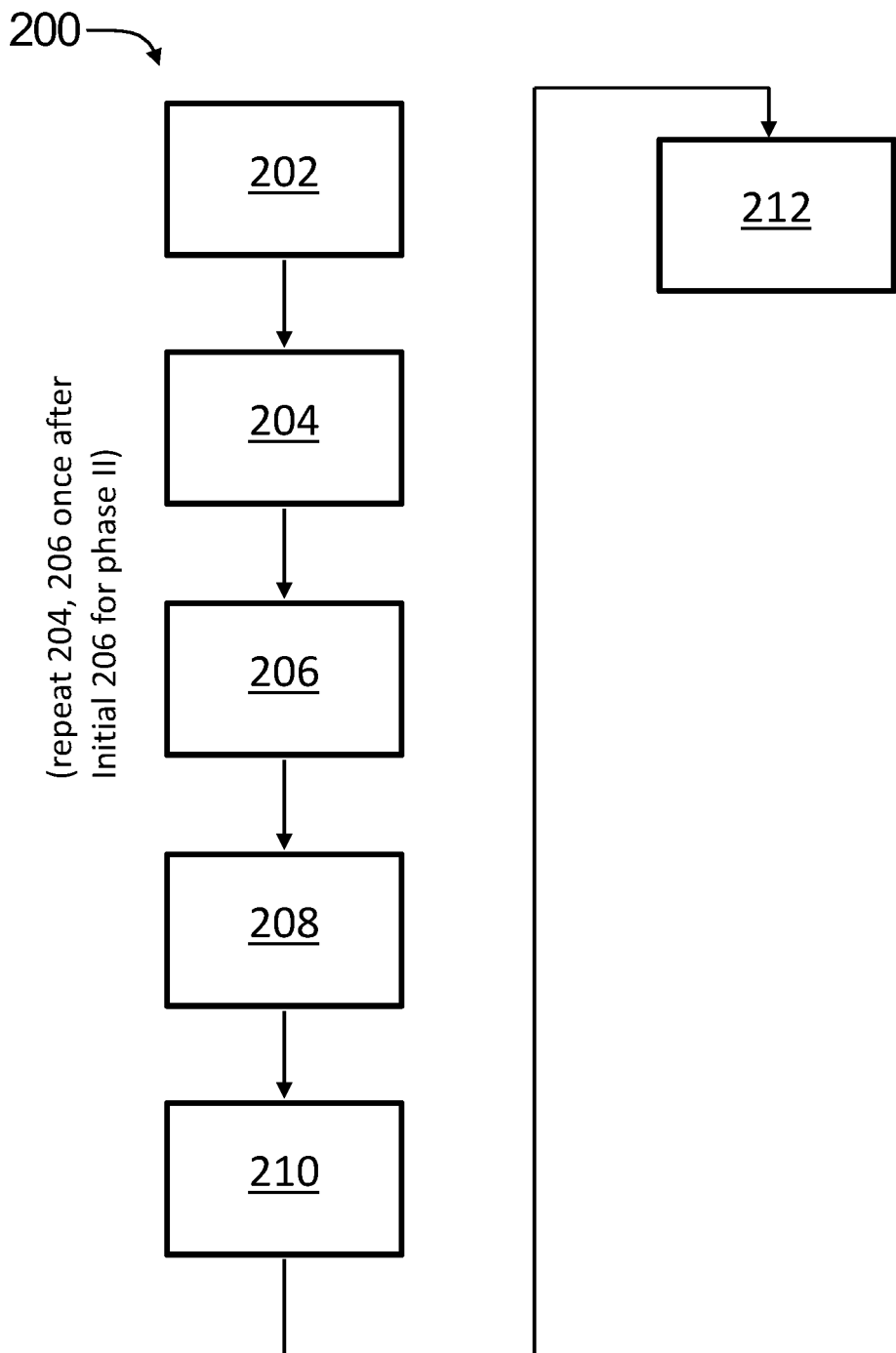
FIG. 3 shows example steps of a method according to exemplary embodiments hereof.

In another embodiment as shown in FIG. 3, cannabinoids infused coconut or similar oil, such as the infused coconut oil produced by process 102-114 (FIG. 2) described above, is used to infuse coffee beans or raw nuts with cannabinoids.

First (at 202), at least a portion of the cannabinoids infused coconut oil obtained from 102-114 (FIG. 2) is heated to a first temperature equal to or between 175° F. and 189° F.

Next (at 204), a selection of coffee beans or raw nuts is added and stirred into the mixture and held at the first temperature (e.g., preferably about 175° F. to 189° F.) for about 5-6 hours. In the case of coffee beans, the beans preferably are used two or more days after roasting of the beans to allow for chemical release (degassing) of the coffee beans. For the purposes of this specification, the term "about" used in relation to periods of time will mean ±3%.

Next (at 206), the mixture of the coffee beans or raw nuts and infused oil is frozen into a solid, frozen biomass. In one example for a commercial scale, this step can be carried out by covering the mixture in a stock pot with a freezer blanket that will rapidly freeze the mixture and keep it frozen. Alternatively, the material can be rapidly frozen in a blast freezer.

At this juncture, the solid, frozen biomass of coconut oil and coffee beans (or raw nuts) can be processed in one of two ways. First, the coconut oil and coffee beans (or raw nuts) can be heated, strained, and frozen as per steps 208, 210, and 212 to yield cannabinoids infused coffee beans or raw nuts produced by a single round or phase of heating and freezing. Second, the coconut oil and coffee beans or raw nuts alternatively can be treated with a second round or phase of heating and freezing, in which steps 204 and 206 are repeated, followed by subsequent steps 208, 210, and 212 to yield cannabinoids infused coffee beans or raw nuts produced by two rounds of heating and freezing. The single round/phase treatment will produce cannabinoids infused coffee beans or raw nuts having about a 50% relative level of infused cannabinoids compared to a double round/phase treatment that will produce cannabinoids infused coffee beans or raw nuts having about an arbitrary 100% relative level of infused cannabinoids. The double round/phase treatment has been found to provide maximal levels of cannabinoids infused into the coffee beans or raw nuts; these maximal levels are arbitrarily referred to as 100% levels of infused cannabinoids. The single round/phase treatment can produce cannabinoids-infused coffee beans or raw nuts that are adequate for many applications. If higher infused levels of cannabinoids in coffee beans or raw nuts are desired for a particular application, the double round/phase treatment of cannabinoids infused coffee beans or raw nuts can be applied.

Following step 206, at step 208, the mixture including the now infused coffee beans (or raw nuts) and infused oil is heated to a temperature equal to or between 100° F. and 150° F. and held at the temperature for a sufficient period of time to liquefy the oil, typically about 2-4 hours, and preferably for about 2 hours.

After this heating step at 208, the mixture is strained at step 210 (using any suitable straining techniques) and the cannabinoids infused coffee beans or raw nuts are removed from the coconut oil.

Then (at 212), the cannabinoids infused coffee beans or raw nuts are frozen, such as in a blast freezer, and stored frozen for subsequent use/packing/consumption.

This process 202-212 (FIG. 3) results in coffee beans or raw nuts infused with cannabinoids, which can be referred to as cannabinoids infused coffee beans or raw nuts. The whole spectrum cannabinoids infused coffee beans can then be used according to various, typical coffee grinding and brewing methods to produce cannabinoids infused coffee beverages for drinking consumption.

In some embodiments, the freezing step at 206 provides organic pressure to the coffee beans or raw nuts that deepens the physical depth of the cannabinoid infusion into the coffee beans or raw nuts. For example, in some embodiments, the freezing step at 206 causes the cannabinoids to be pressed 10%, 20%, 30%, 40%, 50%, 60%, 70%, 80%, 90% and/or 100% to the center of each coffee bean or raw nut.

It is understood that the acts described above are meant as a general overview and demonstration of an exemplary method, and that the method may include different and/or additional acts as described herein or otherwise.

While the present invention has been described as having particular configurations disclosed herein, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

It is understood that any aspect and/or element of any embodiment of the method(s) described herein or otherwise may be combined in any way to form additional embodiments of the method(s) all of which are within the scope of the method(s).

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

It should be appreciated that the words "first," "second," and so on, in the description and claims, are used to distinguish or identify, and not to show a serial or numerical limitation. Similarly, letter labels (e.g., "(A)", "(B)", "(C)", and so on, or "(a)", "(b)", and so on) and/or numbers (e.g., "(i)", "(ii)", and so on) are used to assist in readability and to help distinguish and/or identify, and are not intended to be otherwise limiting or to impose or imply any serial or numerical limitations or orderings. Similarly, words such as "particular," "specific," "certain," and "given," in the description and claims, if used, are to distinguish or identify, and are not intended to be otherwise limiting.

As used herein, including in the claims, the terms "multiple" and "plurality" mean "two or more," and include the case of "two." Thus, e.g., the phrase "multiple ABCs," means "two or more ABCs," and includes "two ABCs." Similarly, e.g., the phrase "multiple PQRs," means "two or more PQRs," and includes "two PQRs."

The present invention also covers the exact terms, features, values and ranges, etc. in case these terms, features, values and ranges etc. are used in conjunction with terms such as about, around, generally, substantially, essentially, at least etc. (i.e., "about 3" or "approximately 3" shall also cover exactly 3 or "substantially constant" shall also cover exactly constant).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components unless specifically so stated.

It will be appreciated that variations to the embodiments of the invention can be made while still falling within the scope of the invention. Alternative features serving the same, equivalent or similar purpose can replace features disclosed in the specification, unless stated otherwise. Thus, unless stated otherwise, each feature disclosed represents one example of a generic series of equivalent or similar features.

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

Use of exemplary language, such as "for instance", "such as", "for example" ("e.g.,") and the like, is merely intended to better illustrate the invention and does not indicate a limitation on the scope of the invention unless specifically so claimed.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

The invention claimed is:

1. A method of making coffee beans or raw nuts infused with *cannabis* extract comprising:
    (a) providing *cannabis;*
    (b) freezing the *cannabis* to yield frozen *cannabis;*
    (c) providing food grade oil at a temperature of 150° F.-200° F.;
    (d) adding at least a portion of the frozen *cannabis* of (b) to the food grade oil of (c) to form a *cannabis* and food grade oil mixture;
    (e) heating the *cannabis* and food grade oil mixture of (d) to a temperature of 150° F. 200° F. for 5-7 hours;
    (f) freezing the *cannabis* and food grade oil mixture of (e) into a solid, frozen biomass of *cannabis* and food grade oil mixture;
    (g) heating the solid, frozen biomass of *cannabis* and food grade oil mixture of (f) at a temperature of 150° F.-200° F. for 2-4 hours;
    (h) straining the *cannabis* and food grade oil mixture of (g) to separate the food grade oil from the *cannabis* to yield a *cannabis* extract;
    (i) heating the *cannabis* extract of (h) to a temperature of 250° F. to 300° F. for 3-6 hours;
    (j) adding raw nuts or coffee beans to the *cannabis* extract of (i) to form a mixture of coffee beans or raw nuts with the *cannabis* extract;
    (k) heating the mixture of coffee beans or raw nuts and *cannabis* extract of (j) to a temperature of 175° F. F for 5-6 hours;
    (l) freezing the mixture of coffee beans or raw and *cannabis* extract (k) to form a solid, frozen mixture of coffee beans or raw nuts and *cannabis* extract;
    (m) heating the solid, frozen mixture of coffee beans or raw nuts with *cannabis* extract of (l) to a temperature of 100° F.-150° F. to liquify the *cannabis* extract; and
    (n) straining the coffee beans or raw nuts from the *cannabis* extract of (m) to yield *cannabis* extract infused coffee beans or raw nuts.

2. The method of claim 1, further comprising:
    (O) freezing the *cannabis* extract infused coffee beans or raw nuts of step (n).

3. The method of claim 1, further comprising: repeating steps (e) and (f) one or more times before step (g).

4. The method of claim 1, further comprising: repeating steps (k) and (l) one or more times before step (m).

5. The method of claim 1, further comprising: repeating steps (e) and (f) one or more times before step (g); and repeating steps (k) and (l) one or more times before step (m).

6. The method of claim 1, wherein the temperature of steps (C) and (E) are performed at 185° F.

7. The method of claim 1, wherein the *cannabis* provided in (A) is selected from the group consisting of *Cannabis Sativa, Cannabis* Indica, and *Cannabis Ruderalis.*

8. The method of claim 1, wherein the food grade oil provided in (C) is selected from the group consisting of coconut oil, medium chain triglycerides oil, vegetable oil, sunflower oil, olive oil, grape seed oil, butter, shortening, margarine, lard, and a combination thereof.

9. The method of claim 1, wherein the food grade oil provided in (C) is coconut oil.

10. The method of claim 1, wherein the food grade oil provided in (C) is medium chain triglycerides oil.

11. The method of claim 1, wherein the food grade oil provided in (C) is a mixture of coconut oil and medium chain triglycerides oil.

12. The method of claim 1, wherein the food grade oil provided in (C) is a mixture of coconut oil and medium chain triglycerides oil at a ratio ranging from 75% coconut oil:25% medium chain triglycerides oil to 90% coconut oil:10% medium chain triglycerides oil.

13. The method of claim 1, wherein coffee beans are added in (J).

14. The method of claim 1, wherein coffee beans that have been degassed for at least two days following roasting of the coffee beans are added in (J).

15. The method of claim 1, wherein raw nuts are added in (J).

16. The method of claim 1, wherein the *cannabis* and the food grade oil are provided at a ratio of 1 pound of *cannabis* to 2 gallons of food grade oil in (D).

17. The method of claim 1, wherein the *cannabis* and the food grade oil are provided at a ratio ranging from 10%, 20%, 30%, 40%, 50%, 75%, to 100% of 1 pound of *cannabis* to 2 gallons of food grade oil.

18. The method of claim 1, wherein the *cannabis* in (A) is buds of *cannabis*.

\* \* \* \* \*